(12) United States Patent
Green et al.

(10) Patent No.: US 11,543,465 B2
(45) Date of Patent: Jan. 3, 2023

(54) ENCAPSULATION METHODS FOR FLUID-COMMUNICATING MAGNETOELASTIC SENSORS

(71) Applicant: THE REGENTS OF THE UNIVERSITY OF MICHIGAN, Ann Arbor, MI (US)

(72) Inventors: Scott Green, Davison, MI (US); Yogesh B. Gianchandani, Ann Arbor, MI (US); Richard Kwon, Ann Arbor, MI (US); Grace Elta, Ann Arbor, MI (US); Jiqing Jiang, Sunnyvale, CA (US); Ramprasad Nambisan, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 282 days.

(21) Appl. No.: 16/841,323

(22) Filed: Apr. 6, 2020

(65) Prior Publication Data
US 2020/0319268 A1    Oct. 8, 2020

Related U.S. Application Data

(60) Provisional application No. 62/830,151, filed on Apr. 5, 2019.

(51) Int. Cl.
*G01R 33/18*    (2006.01)
*G01R 33/00*    (2006.01)
(Continued)

(52) U.S. Cl.
CPC ............ *G01R 33/0047* (2013.01); *A61F 2/82* (2013.01); *G01R 33/18* (2013.01);
(Continued)

(58) Field of Classification Search
CPC ............... G01R 33/0047; G01R 33/18; G01R 33/3692; A61F 2/82; A61F 2002/825;
(Continued)

(56) References Cited

U.S. PATENT DOCUMENTS

| 7,271,586 B2* | 9/2007 | Bohlinger | G01C 17/28 324/247 |
| 8,212,552 B2* | 7/2012 | Gianchandani | G01R 33/063 324/228 |
| 2006/0287602 A1* | 12/2006 | O'Brien | A61B 5/0031 600/561 |

OTHER PUBLICATIONS

Jiang et al., "Encapsulation Approaches for In-Stent Wireless Magnetoelastic Sensors," IEEE Transactions on Biomedical Engineering, 10 pages (2019).

* cited by examiner

*Primary Examiner* — Jermele M Hollington
*Assistant Examiner* — Taqi R Nasir
(74) *Attorney, Agent, or Firm* — Marshall, Gerstein & Borun LLP

(57) ABSTRACT

Encapsulation packages for stent-deployable monitoring devices formed of resonator sensors and allowing for magnetic biasing elements that exhibit a targeted impact on the mechanical characteristics of a stent are provided. Encapsulation packages are formed of different types and include a longitudinal shield and curved end on profile for aligning the shield within the deployable stent, the shield having perforations such that a resonator can be positioned adjacent the perforations for allowing particulate within the stent to collect and be measured by the resonator during deployment.

12 Claims, 12 Drawing Sheets

(51) Int. Cl.
 *G01R 33/36* (2006.01)
 *A61F 2/82* (2013.01)
 *A61B 5/00* (2006.01)
(52) U.S. Cl.
 CPC ........ *G01R 33/3692* (2013.01); *A61B 5/6862* (2013.01); *A61F 2002/825* (2013.01); *A61F 2250/0058* (2013.01); *A61M 2202/0403* (2013.01)
(58) Field of Classification Search
 CPC .......... A61F 2250/0058; A61B 5/6862; A61M 2202/0403
 See application file for complete search history.

Type H Package

Type HW Package

Type S Package Explosive View

Package Base Top and Bottom Views

Package Cover Top and Bottom Views

Type H Package

Type HW Package

ENCAPSULATION METHODS FOR FLUID-COMMUNICATING MAGNETOELASTIC SENSORS

CROSS-REFERENCE TO RELATED APPLICATIONS

This application claims the benefit of U.S. Provisional Application Ser. No. 62/830,151, filed Apr. 5, 2019, the entirety of which is hereby incorporated herein by reference.

STATEMENT OF GOVERNMENT SUPPORT

This invention was made with government support under DK102663 awarded by the National Institutes of Health. The government has certain rights in the invention.

FIELD OF THE DISCLOSURE

The present disclosure relates generally to wireless sensors in stents and, more particularly, to encapsulation packages for embedding magnetoelastic resonator sensors in stents.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Stents are tubular implanted devices meant to prop open a constricted vessel or duct. Stents are typically formed of a metal or plastic and are typically configured for particular applications and particular vessels.

While stents relieve patients from suffering constriction, stents are not a perfect long-term solution. Indeed, the effectiveness of stents can degrade over time. As a result, stents should be monitored because accumulation of tissue and/or other biomass can block the stent after an unpredictable period of time. Current practices for monitoring stent blockage are indirect, invasive, and/or expensive; they include blood tests, magnetic resonance imaging, and angiography/cholangiography. The shortcomings of current practices often lead to mistimed therapeutic actions, including preemptive and unnecessary invasive procedures and post-symptomatic stent replacement.

An approach to stent monitoring has been through the use of a direct wireless monitoring system. U.S. Pat. No. 8,212,552 discusses stents that have wireless magnetoelastic sensors integrated into the internal lumen of the stent. The sensor mechanically vibrates in response to the application of an oscillating magnetic field from a coil external to the patient. The mechanical vibration of the sensor generates an oscillating magnetic flux that can be measured with a second external coil. The frequency content of the response measured by that second external coil is related to the accumulation of the occlusive biomass, which mechanically loads the sensor. By using a method that is direct and wireless, such techniques have been shown to alter the course of therapy at an earlier junction, preventing the risk of major complications due to stent occlusion.

While stents with integrated wireless sensors have been developed, there is still a need for better performing stents integrated with more accurate sensors. Particularly, given the small scale size of many stents, having a stent and sensor design that is able to withstand deployment while maintaining mechanical performance and wireless signal strength continues to challenge stent designers.

SUMMARY OF THE INVENTION

The present application provides encapsulation packaging and protection of magnetoelastic resonators or other sensors, where such packaging is able to allow fluidic contact between the resonators or other sensors and the surrounding environment during use. The encapsulation packages herein may be used to deploy sensors in stents and in other endoscopic applications. These sensors can be configured in many different types of encapsulation approaches and can be configured for many different types of interrogation applications. Indeed, in various examples, the present techniques are implemented through innovative designs that include encapsulation of the resonator/sensor and associated magnetic biasing elements to protect them during endoscopic deployment. The present techniques include designs that maintain a suitable mechanical configuration of the resonator/sensor and associated magnetic elements and provide high wireless signal strength and sensitivity to accumulation of a pathological characteristic.

In accordance with an embodiment, an encapsulation package for use in a stent, the encapsulation package comprises: a shield extending longitudinally and having a curved end on profile for aligning the shield within the deployable stent, the shield having perforations extending between in inner surface of the shield and an outer surface of the shield; a resonator positioned at the outer surface of the shield and positioned adjacent the perforations for allowing particulate within the stent to collect and be measured by the resonator during deployment; and a frame configured to mount the resonator to the shield. In accordance with an example, the frame is configured to increase stiffness of that encapsulation package while maintaining elasticity of the stent during deployment.

In accordance with an embodiment, an encapsulation package for use in a stent, the encapsulation package comprises: a shield extending longitudinally and having a curved end on profile for aligning the shield within the deployable stent, the shield having perforations extending between in inner surface of the shield and an outer surface of the shield, the shield having one or more channels extending longitudinally on the outer surface with a support wire within each channel and the shield having a cavity; and a resonator positioned within the cavity adjacent the plurality of perforations for allowing particulate within the stent to collect and be measured by the resonator during deployment. In accordance with an example, the support wires and channels are configured to increase stiffness of that encapsulation package while maintaining elasticity of the stent during deployment.

In accordance with an embodiment, an encapsulation package for use in a stent, the encapsulation package comprises: a shield extending longitudinally and having a curved end on profile for aligning the shield within the deployable stent, the shield having a plurality of perforations extending between in inner surface of the shield and an outer surface of the shield and align longitudinally, the shield having a cavity extending along the perforations and two opposing slots on each end of the cavity for mounting a biasing magnet in each slot; and a resonator positioned within the cavity of the shield and positioned adjacent the perforations for allowing particulate within the stent to collect and be measured by the resonator during deployment.

In accordance with an embodiment, an encapsulation package for use in a stent, the encapsulation package comprises: a package cover having a tubular shape, the package cover comprising a plurality of perforations extending between in an inner surface of the package cover and an outer surface of the package cover and extending along a longitudinal axis of the package cover, the package cover further comprising grooves at opposing ends of the package cover and a slot adjacent the plurality of perforations; a package base comprising a cavity and tongues at opposing ends, each tongue configured to engage a respective groove for mounting the package base to the package cover and positioning the cavity adjacent the plurality of perforations; a resonator positioned within the cavity and extending into the slot of the package cover such that the resonator is positioned adjacent the perforations for allowing particulate within the stent to collect and be measured by the resonator during deployment; and a magnetic cuff comprising magnetic struts and at least one magnetic mounting ring for mounting the magnetic cuff to the outer surface of package cover.

In accordance with an example, a stent with integrated encapsulation package, the stent having a casing with an outer sidewall and an inner sidewall, the stent comprises: a cavity integrally formed in the casing of the stent and extending longitudinally along an axis of the stent and extending from of outer sidewall to the inner sidewall; one or more channels formed in the outer sidewall extending longitudinally along the axis, wherein at least one of the one or more channels is adjacent the cavity, and wherein each channel contains a support wire extending longitudinally along the axis; a resonator positioned within the cavity such that the resonator is exposed to particulate within the stent for measurement during deployment; and a cover affixed to the outer sidewall and configured to seal the resonator within the cavity to prevent particulate from exiting the stent through the cavity during deployment.

In various embodiments herein, the resonator is configured to be a sensor, for example, a wireless sensor, within a deployable stent.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

In some examples herein, the present techniques include stent-deployable monitoring devices formed of resonators/sensors characterized by miniaturization fabrication techniques and that have associated magnetic biasing elements that exhibit a targeted impact on the mechanical characteristics of a stent while also maintaining high wireless signal strength.

In some examples herein, the present techniques include stent-deployable monitoring devices formed of resonators/sensors characterized by an encapsulation and associated magnetic biasing elements to protect them during endoscopic deployment of a stent and to maintain a suitable mechanical configuration of the elements to provide high wireless signal strength and sensitivity to accumulation of a pathological characteristic.

In some examples herein, the present techniques include stent-deployable monitoring devices formed of resonators/sensors characterized by enhanced wireless signal strength in an external interrogation module.

The present techniques provides numerous examples of encapsulation of resonators/sensors for using in stent-deployable monitoring devices. Without appropriate encapsulation, the resonators/sensors may be left exposed in the stents and therefore highly likely to be snagged, crimped, or crushed by delivery tools during implantation. To overcome these challenges, a number of different encapsulation techniques have been developed, each allowing for endoscopic deployment of stents of any number of types, including instrumented plastic biliary stents. In various examples, the encapsulation techniques 1) protect the resonator/sensor from being damaged by the introducer—a standard component of the endoscopic delivery, 2) provide mechanical stability to the resonator/sensor during the bending experienced during endoscopic delivery, 3) provide features that allow interaction between the resonator/sensor and the fluids and biomass within the stent, and 4) accommodate permanent magnets to provide a stable DC bias and thus establish a more integrated sensor module.

Figure 1:
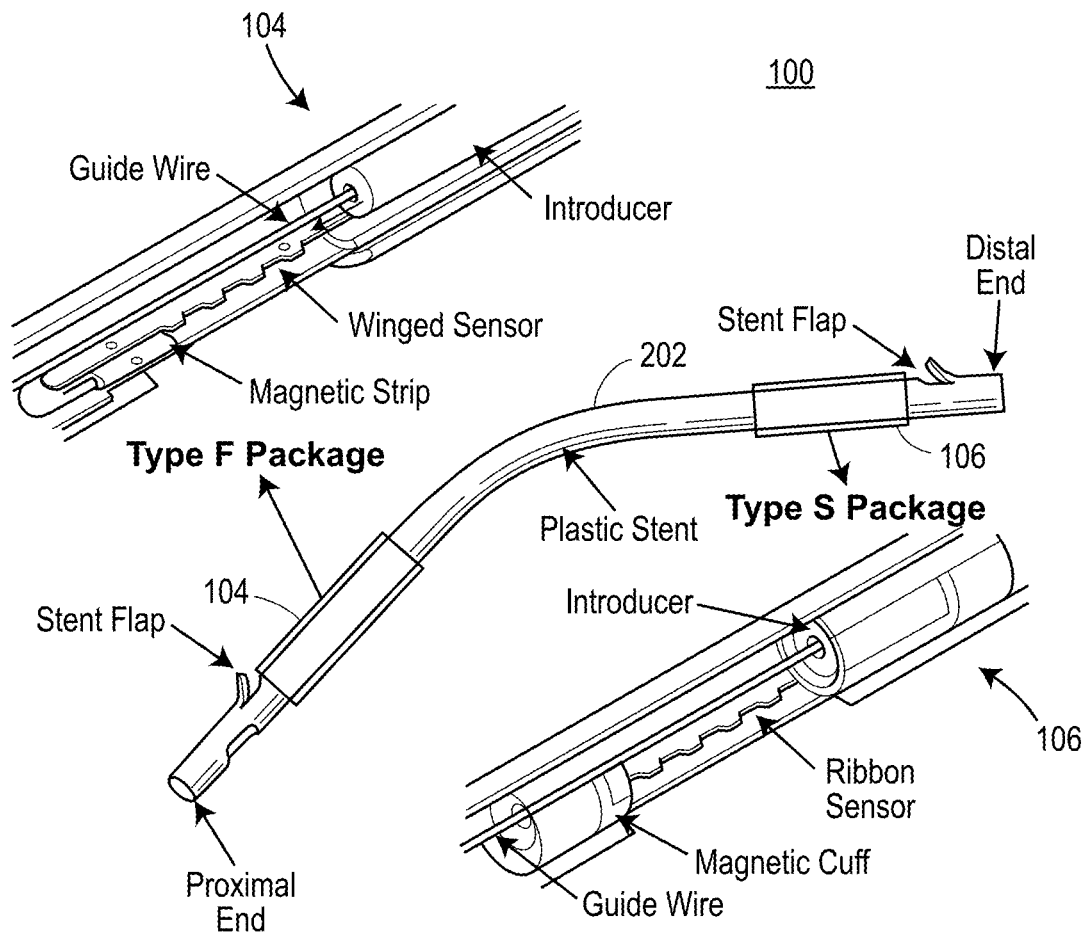
FIG. 1 illustrates an example stent having two different wireless sensors, each having a different encapsulation packaging, in particular an Type F package and a Type S package, in accordance with an example.

FIG. 1 illustrates a stent configuration 100 formed of a plastic stent 102, which may be inserted into a patient through any known stenting techniques. The plastic stent 102 is shown having two different sensors 104 and 106, each adjacent to a proximal end or a distal end, respectively. The plastic stent 102 may be a flexible stent, for example. The plastic stent 102 may have stent flaps at each of the proximal and distal ends. The sensor 104 is configured in a first example encapsulation configuration termed herein a Type F package encapsulation. The sensor 106 is configured in a second example encapsulation configuration termed herein a Type S package encapsulation. FIG. 1 illustrates an expanded cut-away view of each configuration.

As shown, for the sensor 104, the Type F package (representing a mechanically flexible package architecture) encapsulates a winged sensor and two magnetic strips, and can be assembled near the proximal end of a plastic biliary stent 102. The sensor 104 is shown in relation to the guide wire and introducer that are both used for deployment and positioning of the stent 102 in a vessel of a subject.

For the sensor 106, the Type S package (representing a mechanically stiff package architecture) encapsulates a ribbon sensor and is mounted by a magnetic cuff, and can be assembled near the distal end of the stent.

Figure 2:
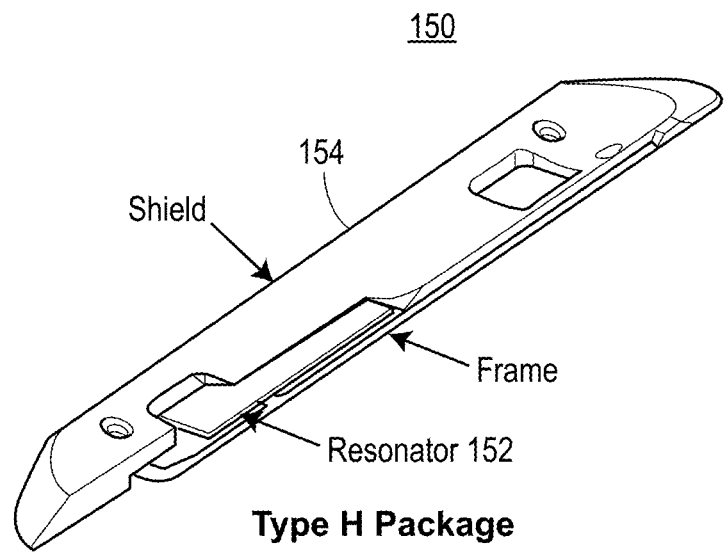
FIG. 2 illustrates an example Type H encapsulation package that can be used with a wireless sensor for a stent, in accordance with an example.
Figure 3:
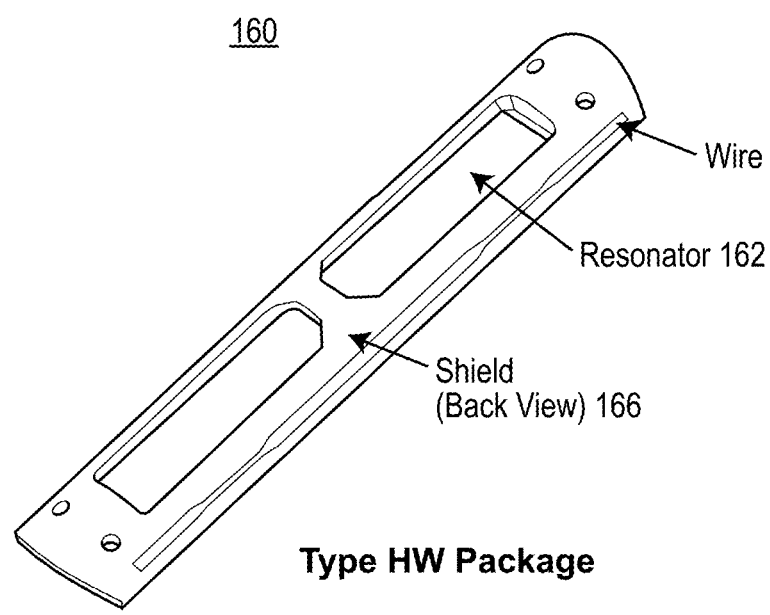
FIG. 3 illustrates an example Type HW encapsulation package that can be used with a wireless sensor for a stent, in accordance with an example.
Figure 4:
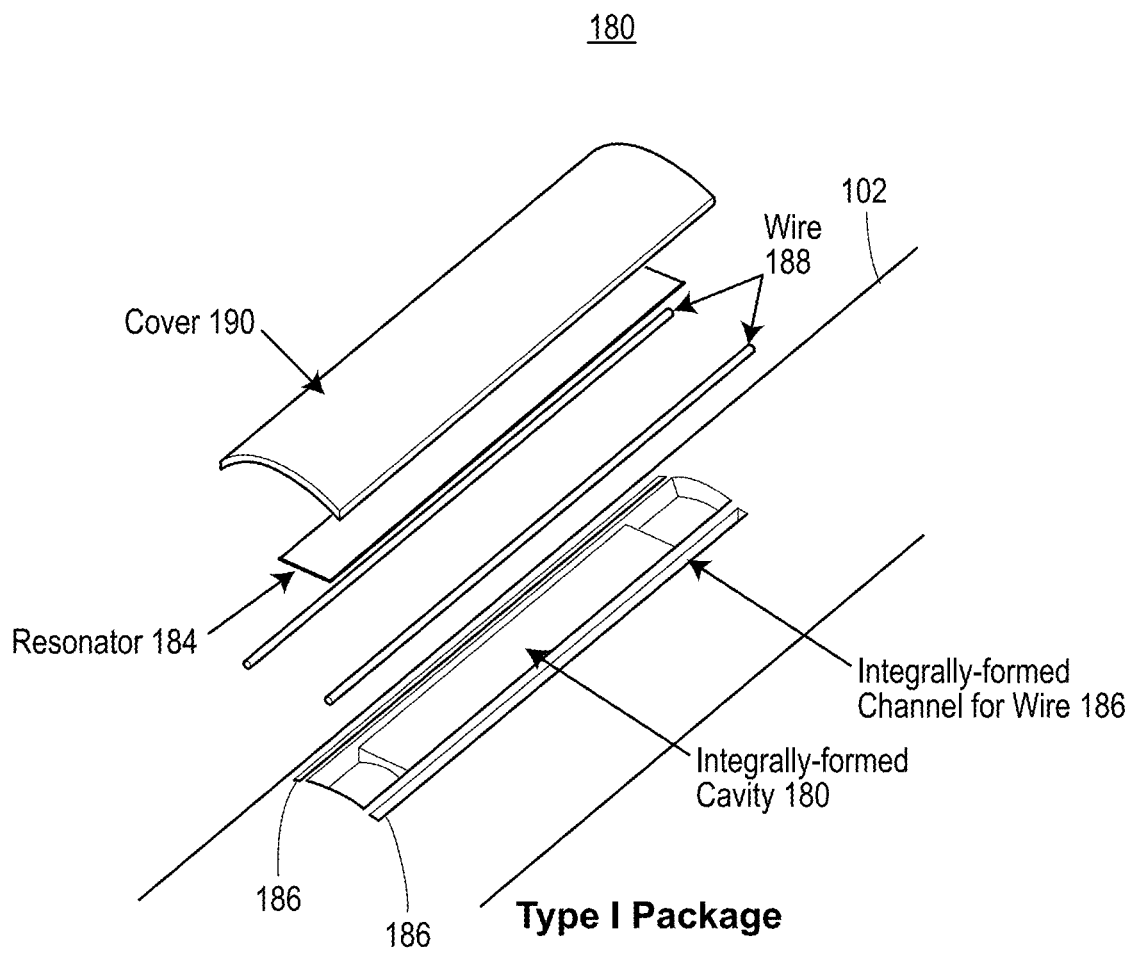
FIG. 4 illustrates an example Type I encapsulation package that can be used with a wireless sensor for a stent, in accordance with an example.

FIGS. 2-4 illustrate other example encapsulation configurations, respectively. FIG. 2 illustrates a Type H package (representing a hybrid material package architecture) 150 that encapsulates a resonator sensor 152 and magnetic bias, where portions of the package are made from different materials. A shield 154 is provided to house, support, and protect the resonator sensor 152 within the stent 102.

FIG. 3 illustrates a Type HW package 160 similar in approach to the Type H package in FIG. 2, in that the Type HW encapsulation an additional material (preferably metal, and preferably a metal with high elasticity, such as Elgiloy or Nitinol) to stiffen the package 160 while maintaining good elasticity to recover its shape after passing through the endoscopic or catheter-based delivery. A resonator sensor 162 is provided within a shield 166 of the Type HW package 160. In the Type HW package 160, this additional material takes the form of wires residing in channels alongside a resonator cavity 164, as shown, for example, along the outer walls of the stent. The Type H package 160 includes a reservoir and an opening showing the resonator sensor 162 mounted on an undersurface of the sensor, as shown. The grooves may be formed on the outer shell of the Type HW package, as further shown in FIG. 9.

FIG. 4 illustrates another example encapsulation configuration, termed a Type I package 180. The Type I package 180 has an integrally-formed cavity 182 for a resonator sensor 184 (and features for other components, such as channels for stiffening wires), where that cavity is formed out of a sidewall of the polymer stent 102. Portions of the cavity are fully cut through the sidewall to allow the resonator 184 (and thus the sensor) to interact with biological fluids and biomass internal to the stent. Integrally-formed channels 186 are provided for receiving and maintaining stiffening wires 188, also shown. After assembling the components (resonator, magnets, and/or wires, etc.) into these features, a cover 190 (of the same material as the stent, or of a similar thermoplastic polymer) can be affixed to the outer surface of the stent to seal the components inside. This affixing process could be achieved preferably by thermally staking (locally melting) the cover into the stent material, but could also be achieved with an appropriate adhesive or other means.

While the examples of FIGS. 1-4 show that the features illustrated do not protrude into the inner lumen of the stent 102, in other examples, the configurations may provide some protrusion to fit all components and to provide room for the cover to not protrude outside the outer diameter of the stent 102.

In various examples, the material for the different encapsulation packaging in FIGS. 1-4 is biocompatible, chemically inert at body temperature, and electromagnetically transparent. Further the encapsulation packaging material should facilitate integration of the features with high resolution (a few hundreds of microns). Once assembled into the stent, the encapsulation packaging material is to be capable of passing through the endoscope during delivery without impeding the capability of the endoscopist to place the stent as desired.

Figure 5A:
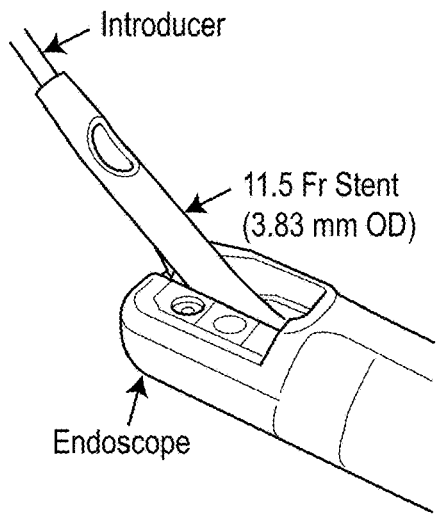
FIGS. 5A and 5B illustrate an endoscope for deploying a stent, the endoscope being shown in lowered position (FIG. 5A) and raised at maximum angle (FIG. 5B) position, in accordance with an example.
Figure 5B:
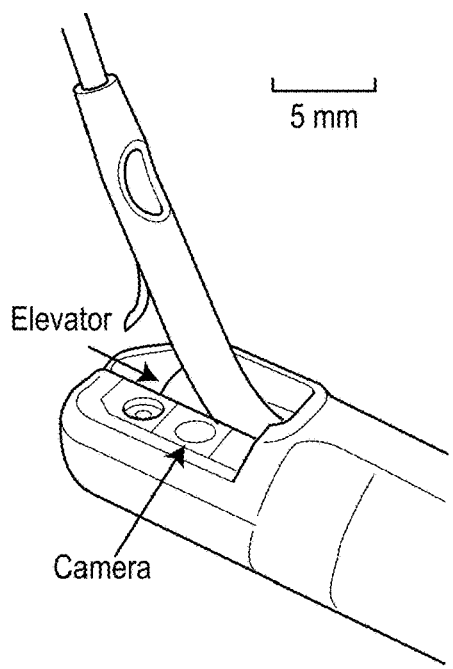
Figure 5C:
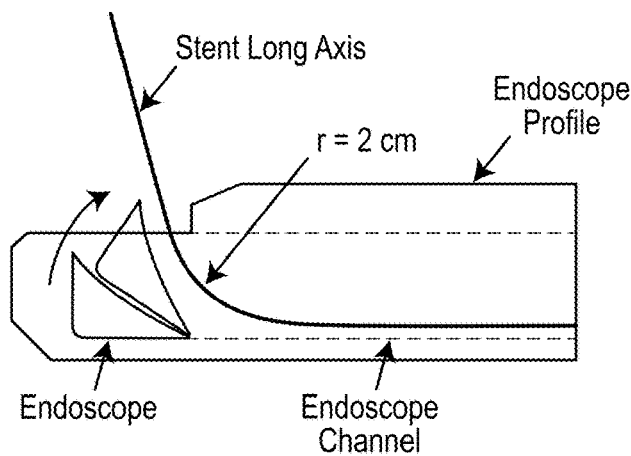
FIG. 5C is a schematic illustration of the endoscope profile and the estimated minimum radius of curvature of the stent, in accordance with an example.

In example implementations, stents from Cotton-Leung Biliary Stents (Cook Group, G22056 and G21847) were used and tested with the encapsulation techniques herein. These stents have the outer diameters of 0.33 cm (10 Fr) and 0.38 cm (11.5 Fr), respectively. The lengths were 7 cm and 9 cm, respectively. A standard endoscopic procedure typically requires the aid of a side-viewing endoscope, which has a camera to locate the position of the biliary orifice and an elevator to adjust the direction of the stent. An example configuration is shown in FIGS. 5A and 5B, which show the elevator of an endoscope lowered and raised, respectively. FIG. 5C is a schematic of the endoscope profile demonstrating the elevator in a lowered position or in a raised position. In operation, when the elevator is lowered, the stent (and packaged sensor) are to pass through a radius of curvature of approximately 7.2 cm. When the elevator is raised, the stent (and packaged sensor) are to survive a radius of curvature of approximately 2 cm. Once the proximal end of the stent is aimed at a biliary orifice, the elevator can be lowered for a smoother delivery and the stent is then pushed into the bile duct by the introducer assembly. Therefore, the front (proximal) part of the stent is to maintain flexibility, whereas the flexibility of the latter (distal) part of the stent may have less to no flexibility, depending on the design. Correspondingly, we determined that in some examples, the flexible Type F encapsulation package may be used near the proximal end of the stent 102, while the stiff Type S package may be appropriately placed near the distal end of the stent 102 (i.e., the end that is located in the duodenum), as shown in the configuration 100 of FIG. 1.

Figure 6:
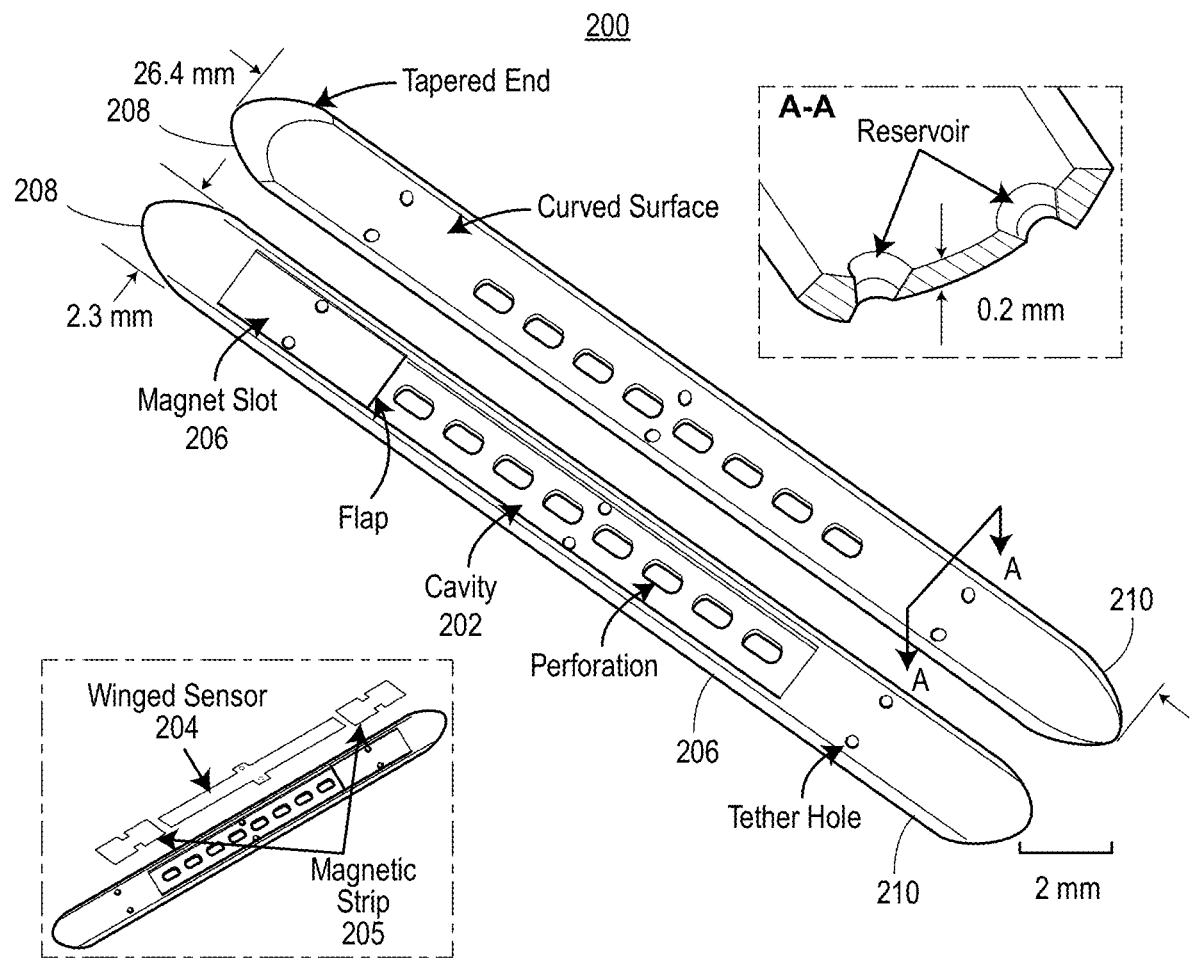
FIG. 6 is detailed illustration of a Type F encapsulation package for a wireless sensor, in accordance with an example.
Figure 7A:
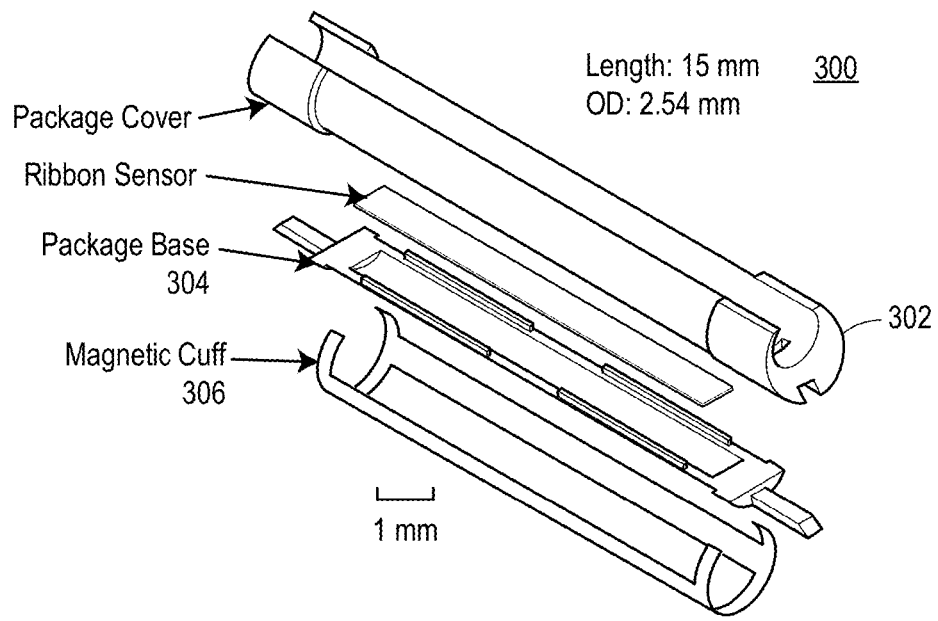
FIGS. 7A-7E are detailed illustrations of a Type S encapsulation package and wireless sensor, showing components thereof, in accordance with an example.
Figure 7B:
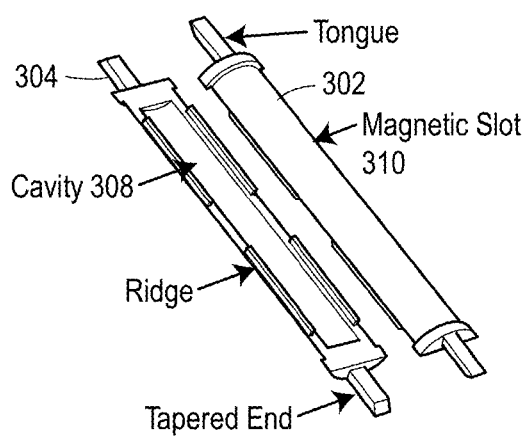
Figure 7C:
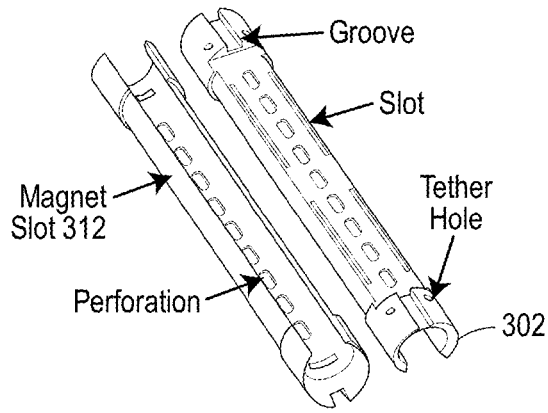
Figure 7D:
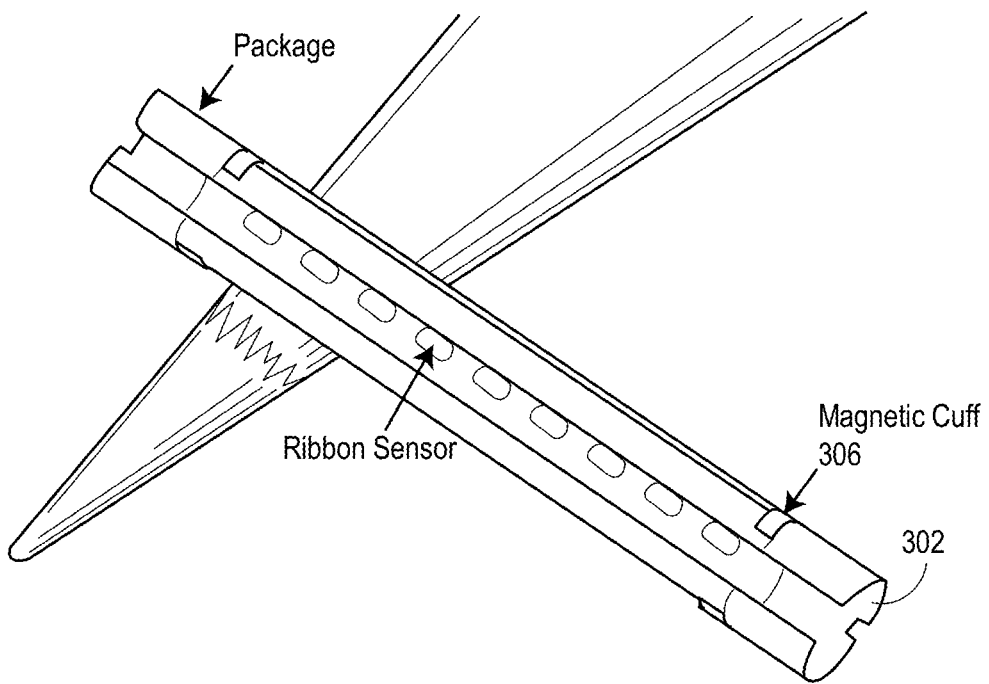
Figure 7E:
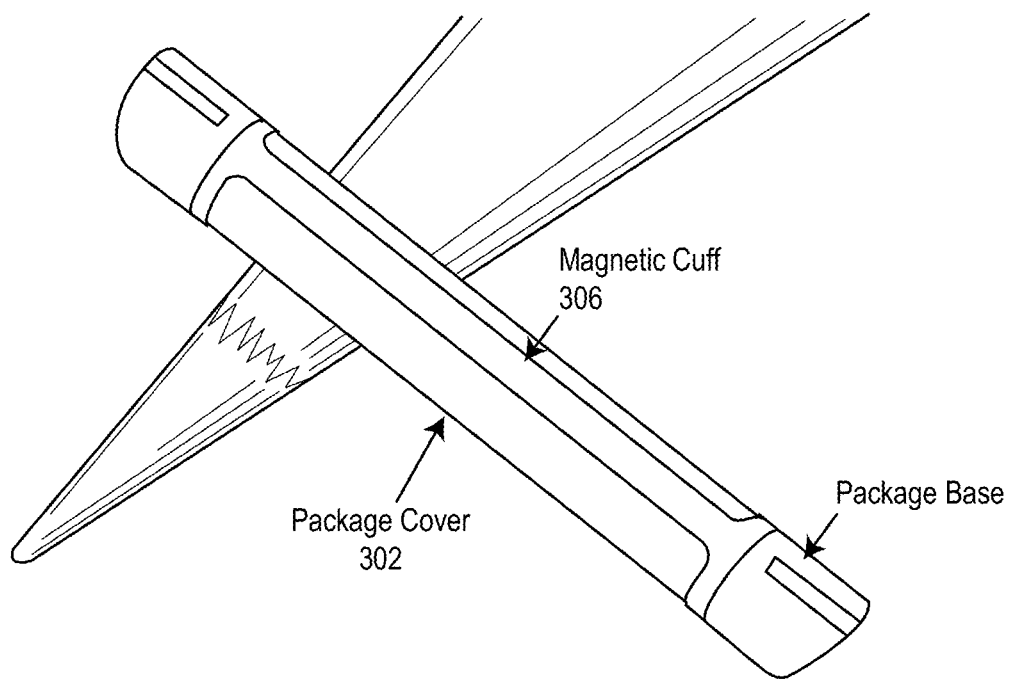
Figure 8:
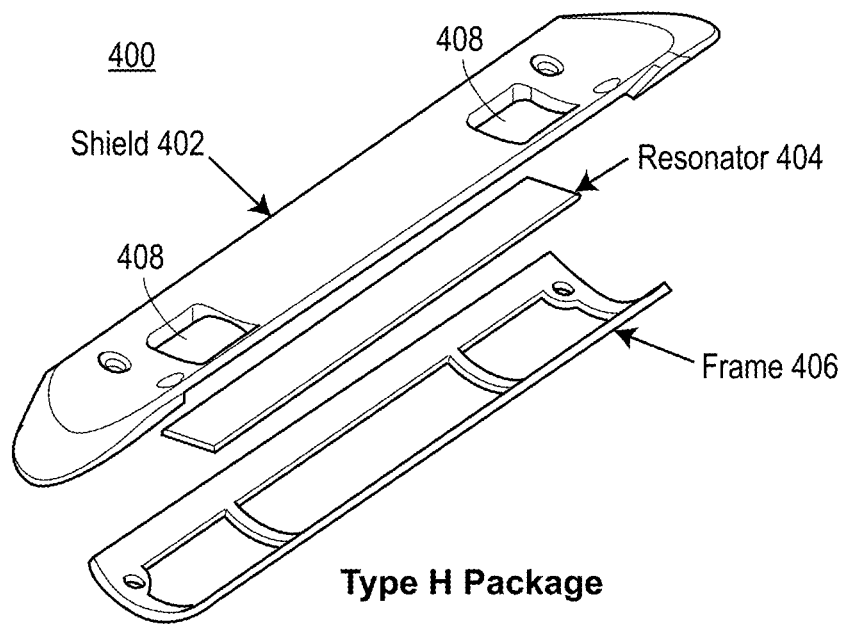
FIG. 8 is a top view of a detailed illustration of a Type H encapsulation package for a wireless sensor, in accordance with an example.

FIGS. 6-8 illustrate detailed examples of Type F, Type S, and Type H/HW encapsulation packages, respectively, in accordance with some examples. Generally speaking, the package types differ in their bending flexibility, with the Type F package intended to be flexible and the Type S and Type H/HW packages intended to be relatively rigid. Different package types will add different amounts of stiffness to that of a bare stent, and that stiffness will depend upon package aspects, such as total length, perforation size and location, the resonator/sensor cavity, etc. Example added stiffnesses include 1-10%, 10-20%, 20-30%, 30%-40%, 40%-50%, 50%-60%, 60%-70%, up to 70-100%, while maintaining sensor operation with bends in the stent. Common features in each package type include a perforated cavity in which to place the sensor while allowing vessel fluid and other particulates (e.g., bile and sludge) to interact with the sensor, tapered ends and curved surfaces to guide the introducer over the package smoothly, and tether holes that facilitate stitching with polyethylene thread the components and the package into the stent.

FIG. 6 illustrates a Type F encapsulation package 200, shown in top and bottom views. In the illustrated example, the Type F package 200 is a single piece construction formed of a biocompatible plastic. The Type F package 200 has a cavity 202 for receiving a sensor 204, such as a winged sensor, as shown in the inset. Two magnet slots 206 and provided for receiving two opposing magnetic strips 205 for generating a resonance across the sensor in response to an external wireless signal, and as the sensor is under different loads. The cavity 202 may be planar, while the opposing side of the Type F package 200 may have a curved surface to coincide with an endoscope. Tapered ends 208 and 210 are each formed with a curved taper to facilitate movement of the Type F package 200. A plurality of perforations 212 extend axially along the length of the cavity 202 and are proved for allowing particulate to build up on the sensor 204. For example, in some applications, the perforations allow bile and synthetic sludge—injected into the stent—to build up on the sensor and change its frequency response as designed.

In an example implementation, the Type F package 200 was formed having a length of 26.4 mm, a width of 2.3 mm, and thickness of 0.53 mm from peak to peak. The sensor 204 and magnetic strips 205 were assembled in the package 200, as shown in the bottom left inset. The sensor cavity 202 was 13 mm long, 1.2 mm wide, and 0.25 mm deep. Flaps at the two ends of the cavity 202 were used to prevent the sensor 204 from sliding out of the cavity. The two flaps were both 0.45 mm long, 1 mm wide, and only 0.13 mm thick. The two magnet slots 206 were both 4 mm long and 1.7 mm wide for placing the magnetic strips. There are six tether holes and each tether hole has a reservoir (shown in the top right inset) to accommodate reflowed PE material, which forms a recessed head to anchor the tether to the package as well as to provide a smooth profile on the top surface of the package.

FIGS. 7A-7C illustrate a Type S encapsulation package 300. FIG. 7A is an exploded view showing a package cover 302, package base 304 forming a sensor cavity and configured to be contained within the package cover 302, a magnetic cuff 306, and a ribbon sensor. The magnetic cuff 306 is formed of two longitudinally-oriented magnetic strips and two transversely-oriented magnetic rings (or semi-rings), serving also as connector ends and is used to bias the sensor. FIG. 7B illustrates the package base 304 from a top view and a bottom view, showing a sensor cavity 308, magnet slot feature 310, ridge, and tapered ends and tongues. FIG. 7C illustrates the package cover 302 from top and bottom views and showing a magnet slot feature 312, a plurality of axially-aligned perforations, tether holes, grooves for receiving tongues of the package base 304, and a slot that aligns with the cavity 308. When the package base is brought together with the package cover (i.e., through the tongue and groove engagement), the cavity opening faces the slot and the perforations of the package cover 302. Furthermore, the magnet slot feature 310 combines with the magnet slot feature 312 to make one continuous surface on which the magnetic cuff is mounted. In some examples, when combined, these features allow pinning of the magnetic cuff to prevent slipping off the package cover in the axial direction after assembly. FIGS. 7D and 7E illustrate a 3D printed polymer package cover 302 with magnetic cuff 306 attached thereto.

In an example implementation of the Type S encapsulation package 300, the ribbon sensor was encapsulated by the package base 304 and package cover 302. The magnetic cuff was clamped on the package cover 302. The overall length was 15 mm and the outer diameter was 2.54 mm. The top and bottom views of the package base 304 and package cover 302 are shown FIGS. 7B and 7C. The package base included the cavity 308 which was 13 mm long, 1.2 mm wide, and 0.18 mm deep, in which the ribbon sensor (12.5 mm×1 mm×60 µm) was placed and otherwise unconstrained. This configuration is in contrast to the Type F package 200, for example, which utilizes a single-piece package with the sensor anchored to the package by a PE tether. Four 4.5 mm long, 0.15 mm wide, and 0.2 mm thick ridge features and two 1.77 mm long, 0.52 mm wide, and 0.31 mm thick tongue features in the package base 304 were designed to match and interlock with the package cover 302, which has complementary features (slots and grooves). The hollowed area in the package cover 302 was designed to be large enough to let the introducer (Φ1.7 mm) pass through. Both package base 304 and package cover 302 were reduced in diameter by 100 µm in selected areas to form magnet slots for receiving the magnetic cuff.

Figure 9:
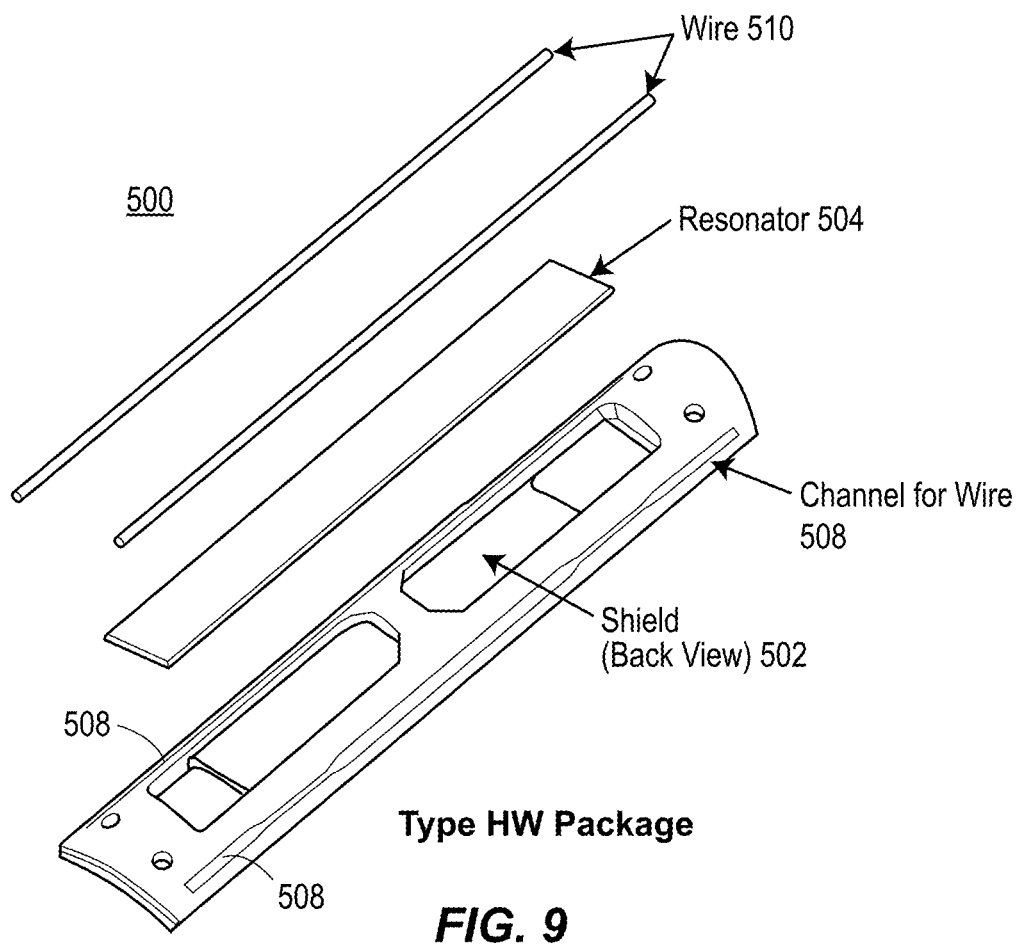
FIG. 9 is a bottom view of a detailed illustration of a Type HW encapsulation package for a wireless sensor, in accordance with an example.

FIGS. 8 and 9 illustrate an example Type H encapsulation package 400 and an example Type HW encapsulation package 500, respectively. Each package is characterized by a having a shield 402 and 502, respectively. The resonator 404 is maintained in engagement with an outer surface of the shield 402 through a frame 406. In some examples, the frame material is metal and preferably a highly elastic metal. The frame may attached to the shield with polyethylene thread through the holes near the ends of the frame (shown) and the shield (shown). In the illustrated example, small transversely-directed struts that cross the frame 406 near its mid-length are used to help pin the resonator 404 into the package for assembly purposes only. There are no specific slots for magnets in this package configuration. The shield 402 has two slots 408 that serve as perforations to allow fluidic communication between the sensor and the stent environment.

The shield 502 (shown in FIG. 9 from a bottom view) may be similar to the shield 402 (shown in FIG. 8 from a top view). In the configuration 500, resonator 504 may be positioned with a slot formed in the shield 502 and adjacent two magnet slots 506. The shield 502 includes two channel 508 for receiving support wires 510, where the support wires facilitate elasticity for movement and sufficient rigidity to maintain stent integrity and operation during deployment. In this way, the wire and channel configuration of the Type HW package 500 performs a similar operation to the frame 406 of the Type H package 400.

The encapsulation package configurations herein may be designed to minimize increases to the flow resistance of the stent. According to Darcy-Weisbach equation, the pressure loss $\Delta P$ in a cylindrical tube of uniform diameter D is proportional to length L:

$$\frac{\Delta P}{L} = \frac{128}{\pi} \cdot \frac{\mu Q}{D^4} \quad (1)$$

where $\mu$ is the dynamic viscosity of the fluid, and Q is the volumetric flow rate. The flow resistance R can be represented as $$R = \frac{\Delta P}{Q} = \frac{128}{\pi} \cdot \frac{\mu L}{D^4} \quad (2)$$

From these expressions the flow resistance change for different encapsulation package types herein can be determined. For example, for a 90 mm long 11.5 Fr stent, the flow resistance change for the entire stent with the Type F package would be approximately +13% assuming the equivalent diameter of the channel which contains the package is 2.4 mm, while that of the stent is 2.63 mm. Similarly, the total flow resistance change for a 70 mm long 10 Fr stent with the Type S package would be approximately +83% when the diameter of the hollowed area is 1.8 mm and the diameter of the stent is 2.53 mm.

The encapsulation packaging approaches in FIGS. 1-9 can have significantly different effects on the bending stiffness of the stent. The calculated bending stiffness of the Type S package does not include the additional magnetic cuff, which, due to the large Young's modulus of the Arnokrome™ 5 material and the geometry of the cuff, adds further stiffness to the Type S package overall.

The encapsulation packages herein may be used implemented with any number wireless sensor designs, including any number of magnetoelastic sensor designs. Magnetoelasticity describes the coupling between stress, strain, and magnetism. When exposed to a time-varying magnetic field, the magnetic domains in a magnetoelastic material tend to rotate and align with the changing field, affecting the strain of the material and causing mechanical vibrations. As a response, the vibrations in the material generate another oscillating magnetic flux, which can be detected by wireless methods. Changes in the density/viscosity of the medium surrounding a magnetoelastic sensor can be measured by the shifted resonant frequency and quality factor of the resonance. For example, in bile duct applications, these resonance characteristics can reflect the bile sludge accumulation and the stent blockage as a pathology progresses over time.

In some examples herein, the sensors were implemented using a two-layer bonded magnetoelastic ribbon-shaped sensor. Ribbon configurations have a high signal-level-to-footprint efficiency, which is valuable for accommodating the size constraints imposed by the biliary stent. The resonant frequency f of the vibration along the longitudinal axis of the unloaded sensor is determined by:

$$f_n = \frac{n}{2L_s}\sqrt{\frac{E_s}{\rho_s}} \quad n = 1, 2, 3 \quad (5)$$

where $L_s$ is the length of the ribbon, $E_s$ is the Young's modulus, and $\rho_s$ is the density of the sensor. In at least some example, the fundamental resonant frequency may be considered (n=1) due to the benefits of larger signal strength and lower frequency (which results in less attenuation through electrically conductive tissue).

Figure 10:
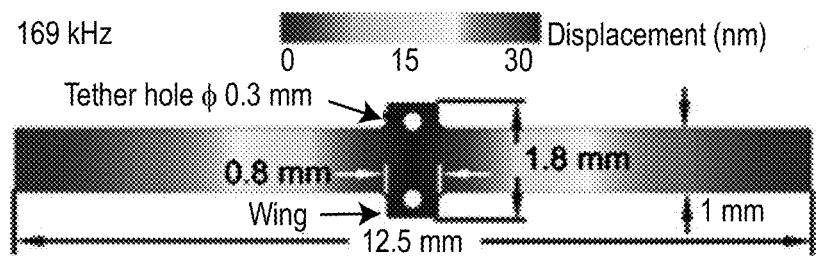
FIG. 10 illustrates a finite element analysis (FEA) simulation result of a winged sensor, used in a Type F encapsulation package, with the wings anchored, in accordance with another example. The winged sensor resonates at 169 kHz in a longitudinal mode shape with a maximum displacement of 30 nm, in this example.

For a 12.5 mm long and 1 mm wide ribbon sensor fabricated from Metglas™ 2826MB ($E_s$=100 GPa, $\rho_s$=7.90 g/cm$^3$), the expected resonant frequency is 168.7 kHz, which is also estimated by the finite element analysis (FEA) result (COMSOL Multiphysics). For the sensor used in the Type F package, for example, two additional 0.8 mm×0.4 mm wing features with two Φ0.3 mm tether holes are in the middle of the sensor for anchoring it in the package with minimum impact on the normal vibration. The maximum displacement of the winged sensor is 30 nm according to the FEA simulations (with a simulated 22.3 A/m interrogation field, FIG. 10), while that of the ribbon sensor shows a similar result of 32 nm at 166 kHz.

Although magnetoelastic transduction is generally nonlinear, it can be treated as linear when small exciting fields are used. For a ribbon sensor, the operating point of the sensor 600 is set by the bias (steady) magnetic field from the magnets 602, 604. An appropriate choice of the operating point can optimize the small-signal magnetostrictivity, and thus maximize sensor vibration and signal amplitude. Additionally, due to the coupling between the magnetism and strain, the bias magnetic field also affects the apparent Young's modulus of the material, the phenomenon which is called the ΔE effect. We have shown that changing the DC bias field or orientation could have a large effect on the resonant frequency. Moreover, the shift of the resonant frequency caused by the change of the bias field may result in misdiagnosis; and therefore we designed examples herein to avoid such issues.

To avoid changes in bias field, we integrated the permanent magnet(s) into the encapsulation package and alongside the sensor, thus providing a constant bias to the sensor regardless of external equipment orientation. Each of the different encapsulation packages are able to achieve constant bias, albeit with different parameters for location and sizing on the magnets and ribbon sensors, in some examples. We determined optimimum sizing and location of the magnets through empirical examination, that included manually cutting prototype magnets of various sizes, magnetizing them using an impulse magnetizer (American Scientific High Strength Magnetizer), and experimentally varying the arrangement between the magnets and the sensor while measuring the sensor response.

For the Type F package, the magnets were located close to the inner sidewall of the stent and sized to be as short as possible to maintain the overall flexibility of the assembly. In an example, two 4 mm×1.5 mm×60 μm Arnokrome™ 5 magnetic strips are designed and placed close to the two ends of the winged sensor for biasing, as shown in FIG. 6. An appropriate distance between the magnets and the sensor was experimentally determined to be 100 μm. Two Φ0.3 mm tether holes in the middle of both magnets are designed for fixing the magnetic strips in the package.

For the Type S package, the DC magnetic bias was provided by two 14 mm×1 mm Arnokrome™ 5 magnetic strips, which were oriented along the length of the package and held in place on the package by transversely-oriented magnet rings that are monolithically formed at the ends of the strips, that entire structure collectively forming the magnetic cuff, as shown in FIG. 7A. In this case, magnetic strips extending between the rings also increased the bending stiffness of the assembly.

The encapsulation packages can be formed from any suitable fabrication technique. Various examples herein were formed using 3D printing techniques, in particular polymer-based 3D printing techniques.

Figure 11:
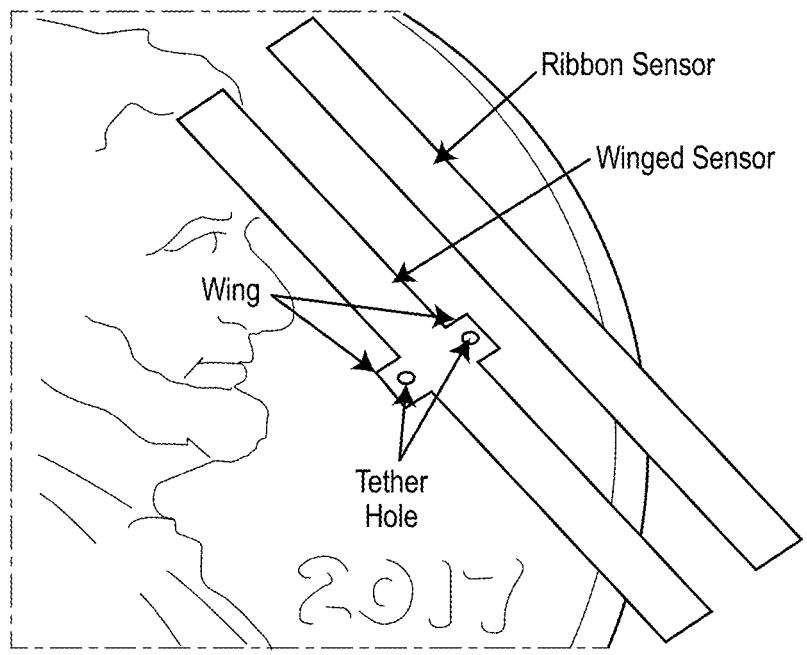
FIG. 11 illustrates an Au—In bonded winged sensor and an Au—In bonded ribbon sensor, formed in accordance with the examples of FIGS. 10 and 11.
Figure 12A:
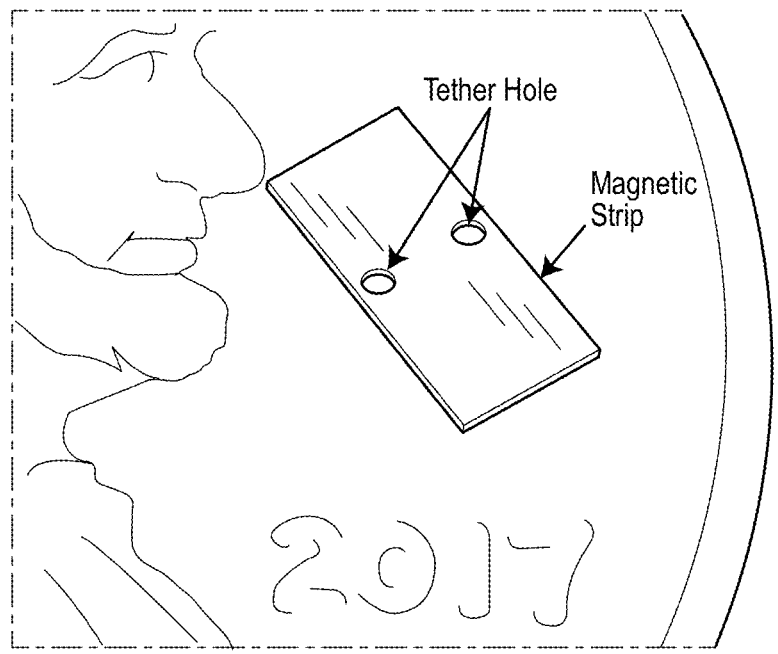
FIGS. 12A and 12B illustrate a microfabricated magnetic strip for an Type F encapsulation package (FIG. 12A), in accordance with an example, and a microfabricated magnetic strip (left) and the magnetic cuff (right) after rolling for an Type S encapsulation package (FIG. 12B), in accordance with an example.
Figure 12B:
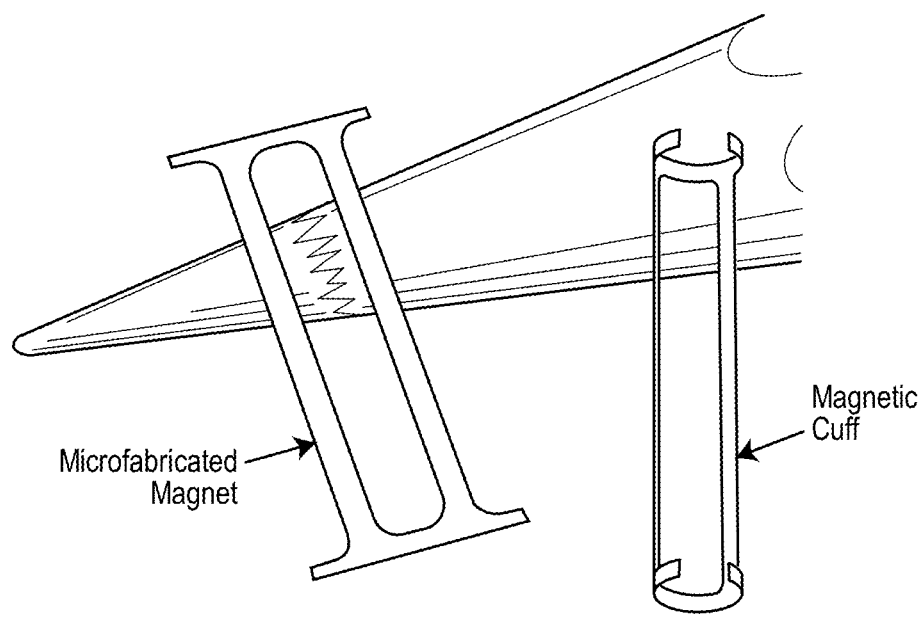

The sensors can be formed of any suitable techniques. In some examples, the ribbon sensors are formed of magnetoelastic sensor material in the form of iron-rich amorphous ferromagnetic alloy Metglas™ 2826MB foil (28 μm thick). In an example, two layers of this foil were bonded together using a gold-indium (Au—In) eutectic bonding process, in order to enable resonators with larger signal without affecting the footprint of the resonators. The bonded Metglas™ foils would then be machined to form winged sensors and ribbon sensors (FIG. 11) by using, e.g., micro electro-discharge machining (μEDM). The μEDM approach can also be used to machine the Arnokrome™ 5 magnetic alloy foils, as shown in FIGS. 12A and 12B.

The stents may be assembled from any suitable process.

Figure 13A:
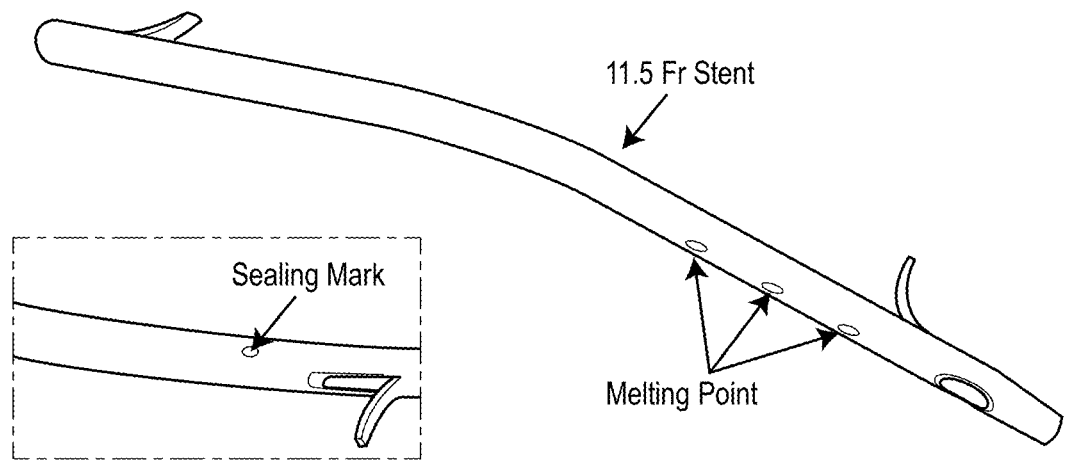
FIG. 13A illustrates a side view of an assembled 11.5 Fr stent with a Type F encapsulation package, in accordance with an example.
Figure 13B:
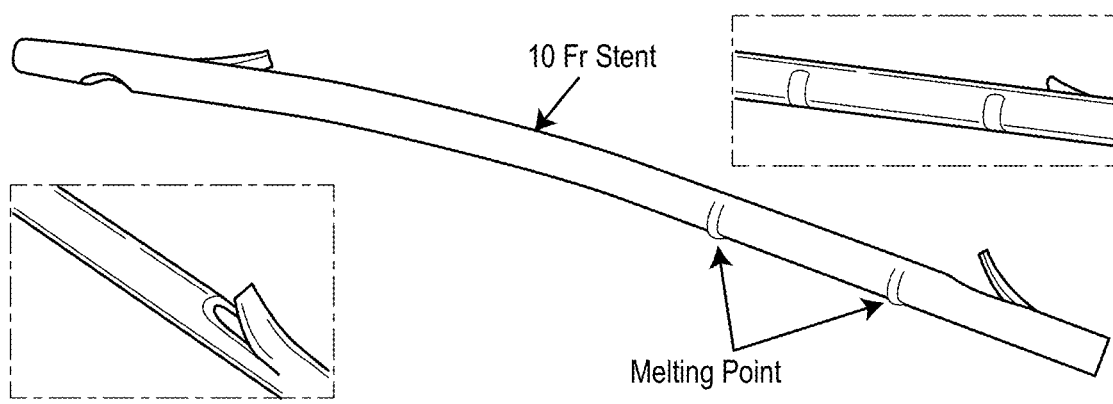
FIG. 13B illustrates a side view of an assembled 10 Fr stent with a Type S encapsulation package, in accordance with an example.

An example assembly process flow for the stent using an Type F encapsulation package was as follows. First, the winged sensor and the two magnets were placed in the proper position of the package (as shown in FIG. 6). Then, six 150 μm diameter PE tethers were threaded through the holes on the package and those on the magnetic strips and winged sensor. The top end of each PE tether was tied to form a square knot and then melted to reflow into the reservoir of the holes. Subsequently, the PE tethers on the package were threaded through holes punched in the stent and were pulled taut to make the package sit close to the inner sidewall of the stent. These tethers were then used to tie three square knots on the outside of the stent. The knots were then melted into the material of the stent. An example, assembled 11.5 Fr stent is shown in FIGS. 13A and 13B.

For the Type S encapsulation package, there were only four PE tethers to be threaded through the holes on the stent, which were close to the distal end of the stent. A 10 Fr stent (Φ2.53 mm) was used, while other processes were similar to that for the Type F package shown in FIG. 13B.

Figure 14:
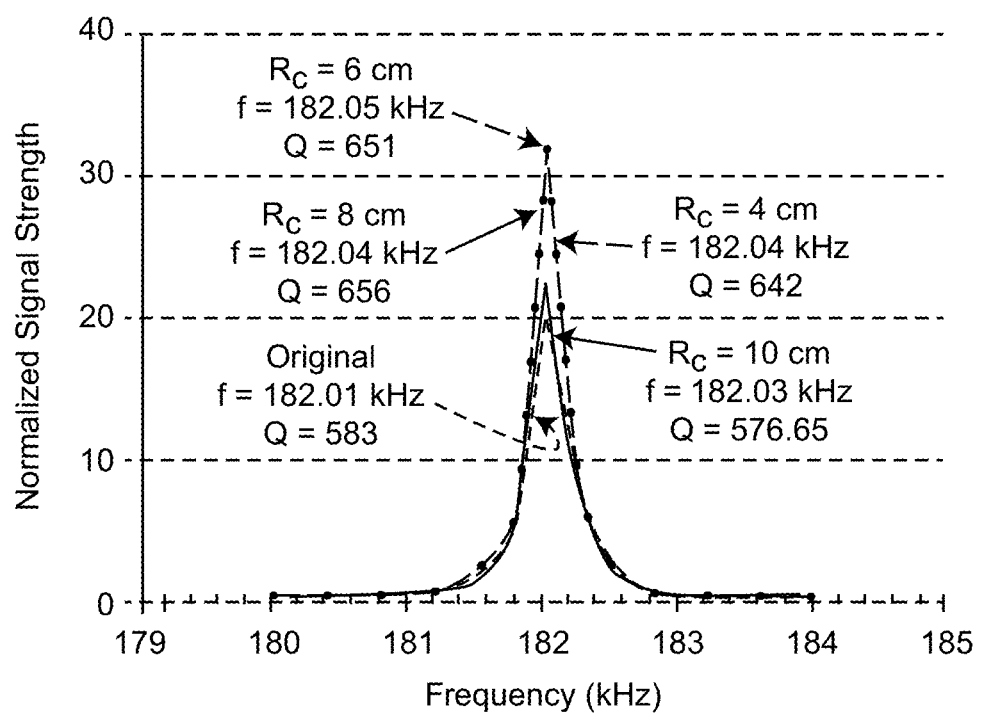
FIG. 14 is a plot of frequency response of sensor in a Type HW package (assembled in stent) while the instrumented stent is bent in the convex direction with various radii of curvature (Rc), in accordance with an example.

In an example, the Type H encapsulation package can be assembled similarly to the Type F package, with the difference being that the tethers are also fed through the metal reinforcing layer of the package. The Type HW encapsulation package assembly can be similar to the Type F package, except that the reinforcing wires are held in place in pre-molded channels within the package. FIG. 14 illustrates a frequency response of an example Type HW encapsulation package, showing consistent frequency response across different radial bends (Rc), demonstrating the consistency and accuracy of sensor operation during normal load and bending conditions. Further, the plot demonstrates that the Type HW encapsulation package is capable of protecting the sensor through intense bending, while retaining a majority of the pre-intense-bending signal strength.

Alternatively, for encapsulation approaches of Types F, S, H, and HW, the package can be made from polyethylene or some other similar thermoplastic material, and portions or all of this package could be melted into the stent to secure the package and its contents.

Assembly with the Type I package is different. Because the cavity and channel features are molded into the stent, the magnetoelastic, magnetic, and reinforcing elements can be dropped into place; then the cover can be sealed onto the outer surface of the stent to secure the elements.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. A encapsulation package for use in a stent, the encapsulation package comprising:
   a shield extending longitudinally and having a curved end on profile for aligning the shield within the deployable stent, the shield having perforations extending between in inner surface of the shield and an outer surface of the shield;
   a resonator positioned at the outer surface of the shield and positioned adjacent the perforations for allowing particulate within the stent to collect and be measured by the resonator during deployment; and
   a frame configured to mount the resonator to the shield.

2. The encapsulation package of claim 1, wherein the frame comprises through holes at opposing ends of the frame for aligning and attaching the frame to through holes in the shield and wherein the frame has transverse struts for mounting the resonator to the shield.

3. The encapsulation package of claim 1, wherein the shield is formed of a biocompatible plastic.

4. A encapsulation package for use in a stent, the encapsulation package comprising:
- a shield extending longitudinally and having a curved end on profile for aligning the shield within the deployable stent, the shield having perforations extending between in inner surface of the shield and an outer surface of the shield, the shield having one or more channels extending longitudinally on the outer surface with a support wire within each channel and the shield having a cavity; and
- a resonator positioned within the cavity adjacent the plurality of perforations for allowing particulate within the stent to collect and be measured by the resonator during deployment.

5. The encapsulation package of claim 4, wherein the shield is formed of a biocompatible plastic.

6. A encapsulation package for use in a stent, the encapsulation package comprising:
- a shield extending longitudinally and having a curved end on profile for aligning the shield within the deployable stent, the shield having a plurality of perforations extending between in inner surface of the shield and an outer surface of the shield and align longitudinally, the shield having a cavity extending along the perforations and two opposing slots on each end of the cavity for mounting a biasing magnet in each slot; and
- a resonator positioned within the cavity of the shield and positioned adjacent the perforations for allowing particulate within the stent to collect and be measured by the resonator during deployment.

7. The encapsulation package of claim 6, wherein the shield is formed of a biocompatible plastic.

8. The encapsulation package of claim 6, wherein the shield comprises curved tapered ends.

9. The encapsulation package of claim 6, wherein the shield comprises through holes having a reservoir to accommodate reflowed material.

10. A encapsulation package for use in a stent, the encapsulation package comprising:
- a package cover having a tubular shape, the package cover comprising a plurality of perforations extending between in an inner surface of the package cover and an outer surface of the package cover and extending along a longitudinal axis of the package cover, the package cover further comprising grooves at opposing ends of the package cover and a slot adjacent the plurality of perforations;
- a package base comprising a cavity and tongues at opposing ends, each tongue configured to engage a respective groove for mounting the package base to the package cover and positioning the cavity adjacent the plurality of perforations;
- a resonator positioned within the cavity and extending into the slot of the package cover such that the resonator is positioned adjacent the perforations for allowing particulate within the stent to collect and be measured by the resonator during deployment; and
- a magnetic cuff comprising magnetic struts and at least one magnetic mounting ring for mounting the magnetic cuff to the outer surface of package cover.

11. The encapsulation package of claim 10, the package cover comprising through hole points at each of the grooves.

12. A stent with integrated encapsulation package, the stent having a casing with an outer sidewall and an inner sidewall, the stent comprising:
- a cavity integrally formed in the casing of the stent and extending longitudinally along an axis of the stent and extending from of outer sidewall to the inner sidewall;
- one or more channels formed in the outer sidewall extending longitudinally along the axis, wherein at least one of the one or more channels is adjacent the cavity, and wherein each channel contains a support wire extending longitudinally along the axis;
- a resonator positioned within the cavity such that the resonator is exposed to particulate within the stent for measurement during deployment; and
- a cover affixed to the outer sidewall and configured to seal the resonator within the cavity to prevent particulate from exiting the stent through the cavity during deployment.

* * * * *